United States Patent [19]

Morris et al.

[11] Patent Number: 4,549,980

[45] Date of Patent: Oct. 29, 1985

[54] WHITE MODIFICATION OF A BIS-TRIAZINYL AMINO STILBENE OPTICAL BRIGHTENER AND A PROCESS FOR MAKING THE SAME

[75] Inventors: Susan M. Morris, John's Island; Thomas J. Thomas; Dietmar Kalz, both of Summerville, all of S.C.

[73] Assignee: Mobay Chemical Corporation, Pittsburgh, Pa.

[21] Appl. No.: 540,748

[22] Filed: Oct. 11, 1983

[51] Int. Cl.[4] .................. C07D 251/54; C09K 11/06; C11D 3/42; D06L 3/12

[52] U.S. Cl. .................. 252/301.23; 8/648; 252/524; 252/543; 544/193.2

[58] Field of Search .................. 252/301.23, 543, 524, 252/102; 8/648; 544/193.2

[56] References Cited

U.S. PATENT DOCUMENTS

| | | | |
|---|---|---|---|
| 3,472,842 | 10/1969 | Hausermann et al. | 260/240 |
| 3,511,833 | 5/1970 | Tscharner | 260/240 |
| 3,684,728 | 8/1972 | Kissling | 252/301.23 |
| 3,895,009 | 7/1975 | Fringeli | 252/301.23 |
| 3,925,260 | 12/1975 | Tscharner et al. | 252/543 |
| 3,951,960 | 4/1976 | Heath | 252/301.23 |
| 3,959,165 | 5/1976 | Yurko | 252/109 |
| 3,994,834 | 11/1976 | Dorlars et al. | 252/543 |
| 4,013,577 | 3/1977 | Wixon | 252/109 |
| 4,082,682 | 4/1978 | Imamorato | 252/92 |
| 4,216,111 | 8/1980 | Thompson | 252/301.23 |
| 4,271,036 | 6/1981 | Uhl | 252/301.23 |
| 4,311,605 | 1/1982 | Eckhardt | 252/102 |
| 4,326,982 | 4/1982 | Neumann | 252/301.23 |

FOREIGN PATENT DOCUMENTS

| | | |
|---|---|---|
| 2061862 | 6/1972 | Fed. Rep. of Germany ...... 252/102 |
| 2110996 | 9/1972 | Fed. Rep. of Germany ...... 252/524 |
| 588059 | 7/1959 | Japan . |
| 773152 | 4/1957 | United Kingdom . |
| 997044 | 6/1965 | United Kingdom . |
| 1173806 | 12/1969 | United Kingdom . |
| 1293804 | 10/1972 | United Kingdom . |

*Primary Examiner*—Dennis L. Albrecht
*Attorney, Agent, or Firm*—Gene Harsh; Joseph C. Gil; Lawrence S. Pope

[57] ABSTRACT

The present invention is concerned with the modification of the sodium salt of a known optical brightener to obtain a white crystalline material. The commercially available 4,4'-bis-(2-anilino-4-phenylamino-1,3,5-triazinyl-6-amino)-stilbene-2,2'-disulphonic acid is neutralized with a sodium base such as caustic and exposed to temperatures above about 65° C. as an aqueous slurry containing some undissolved disodium salt. The water solubility of this salt may be inhibited by the addition of an electrolyte and the product may be recovered by spray drying.

13 Claims, 2 Drawing Figures

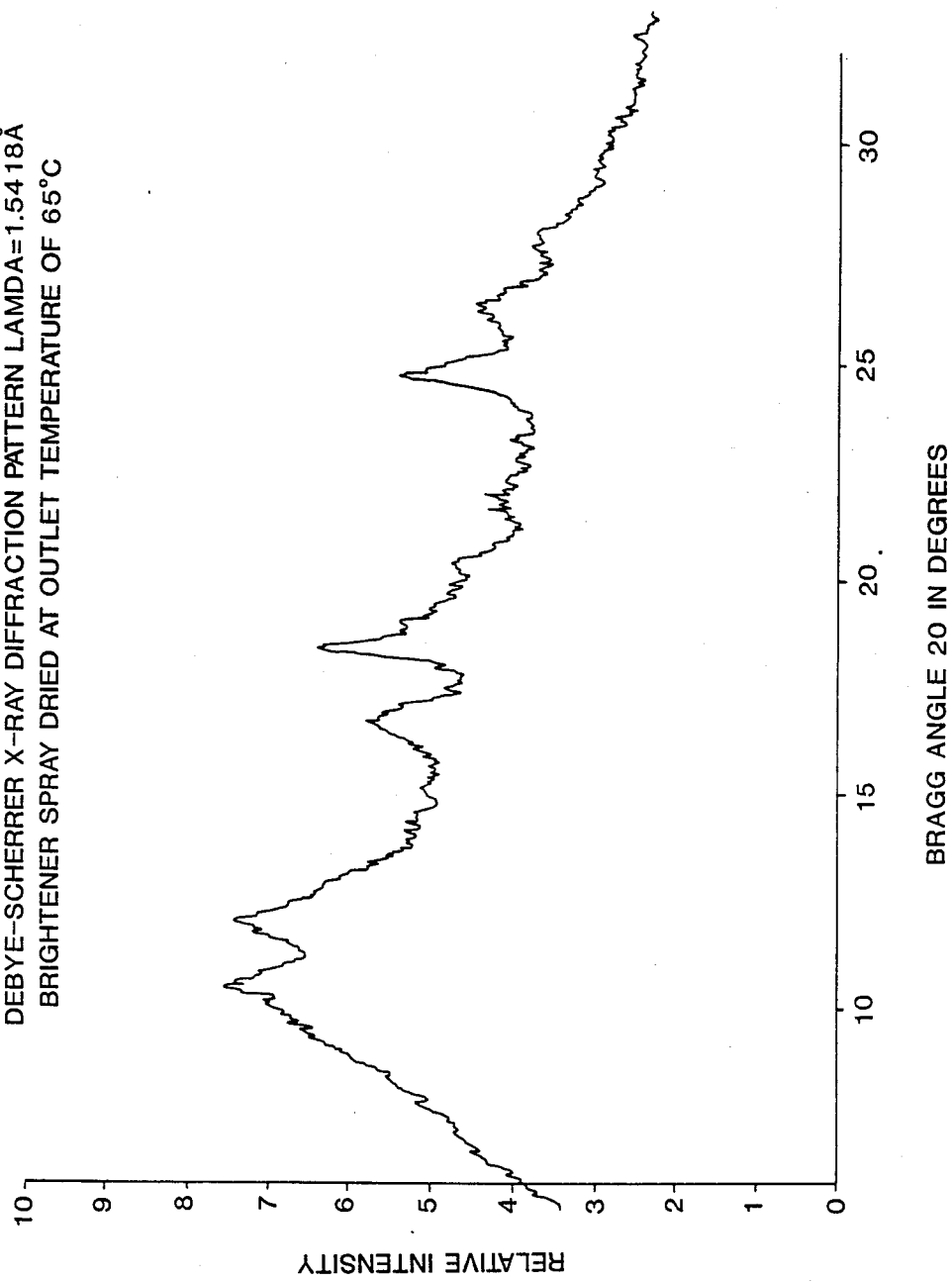

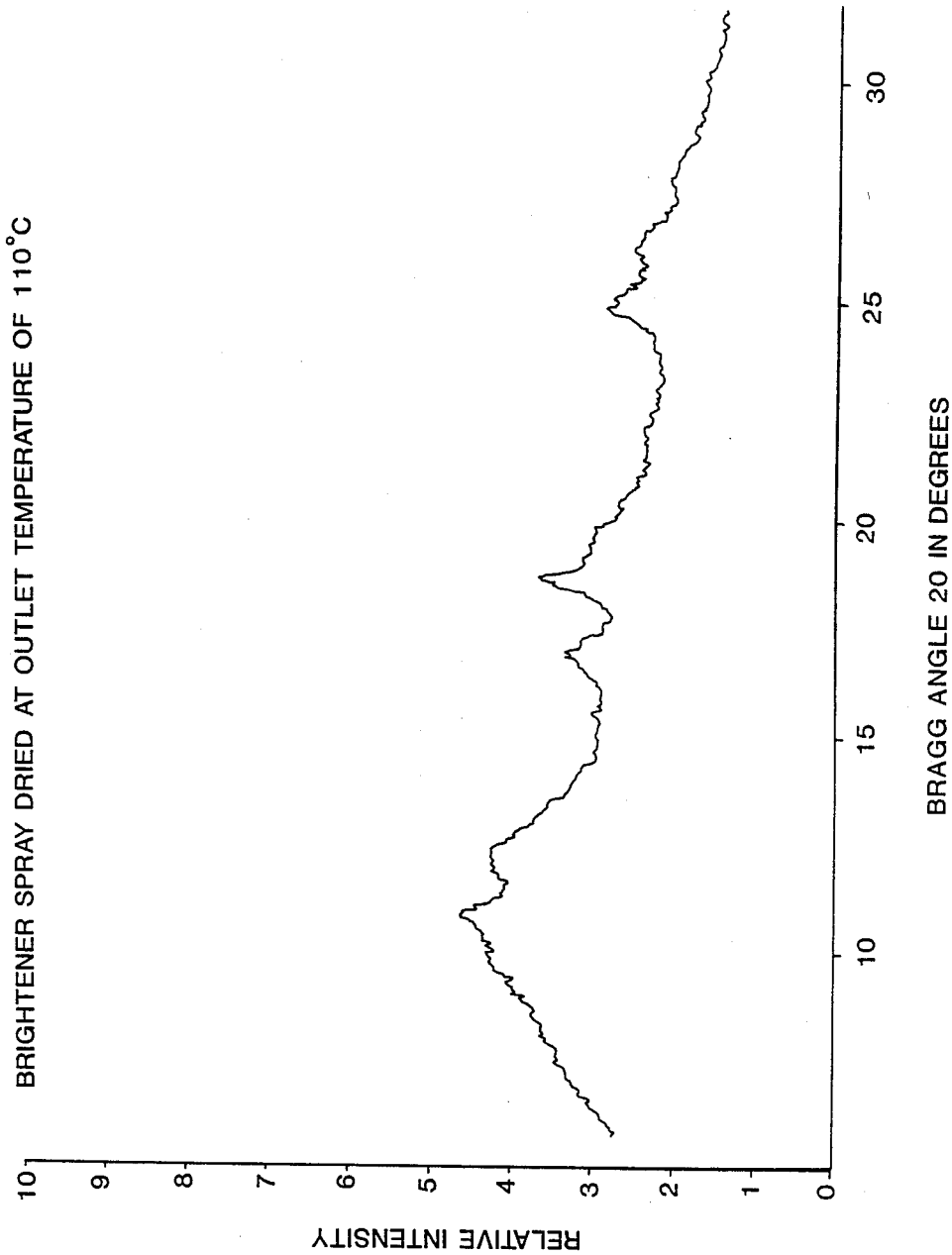

WHITE MODIFICATION OF A BIS-TRIAZINYL AMINO STILBENE OPTICAL BRIGHTENER AND A PROCESS FOR MAKING THE SAME

FIELD OF THE INVENTION

This invention is concerned with modifying a known optical brightener of the bis-triazinyl amino stilbene series to obtain a product which does not objectionably color dry detergent compositions. The chemical and crystal form of this brightener are altered.

BACKGROUND OF THE INVENTION

A series of optical brighteners based on stilbene disulfonic acid including those which are the condensation products of 4,4'-diamino-2,2'-disulphonic acid and cyanuric chloride are well known to the art. These products are utilized by dissolving them into an aqueous medium which is then used to treat the appropriate fiber or fabric. Thus, for many years there was very little interest in the appearance of these brighteners. They were simply powdered industrial products but then the manufactureres of household laundry detergents began to include such materials in their final products.

The use of these optical brighteners in finished customer products created an interest in their physical appearance. There was a concern that the presence of such agents in a detergent composition not discolor the composition. Many of these brighteners had a yellow coloration which they imparted to the detergent compositions into which they were incorporated even when the level of incorporation was fairly low. Typically less than about 0.5 wt. % was used.

Others of these brighteners turned yellow after incorporation into an aqueous slurry of the detergent and drying of the slurry. Household detergent compositions were and still are prepared by the alternative techniques of slurrying the components together and drying them or simply dry blending the components together. Thus, the appearance of these optical brighteners both as produced and after drying from an aqueous slurry became of importance.

Also discoloration of a detergent composition from the addition of an optical brightener was of concern for two major reasons. The detergent manufacturers use the physical appearance of the composition as a criterion of quality control. A discoloration from the optical brightener could make it difficult to detect other problems in the composition such as contamination or degradation of another component. Additionally, the consumer often has a negative reaction to a detergent composition which has any yellow coloration. While this is admittedly a physiological factor actually not related to the ultimate performance of the detergent composition in cleaning clothes, it does substantially effect the salability of such products.

It was discovered that both of these discoloration phenomena could be favorably affected by modifying the crystal form of these optical brighteners. Unfortunately but not unexpectedly the conditions necessary to obtain a favorable modification were not universal. It appears that each particular optical brightening compound may require its own unique conditions.

United Kingdom Pat. No. 997,044 discloses the crystal modification of the neutralized form of 4,4'-bis-[2'',4'''-(diphenylamino)-s-triazinyl-(6''')-amino]stilbene-2,2'-disulfonic acid by heating between 100° and 200° C. at between 5 and 225 psig in the presence of an alkaline material. A material which is yellow or has a strong tendency to turn yellow is reportedly converted into a stable white material.

U.S. Pat. No. 3,472,842 discloses the crystal modification of the structurally similar neutralized 4,4'-bis-[2''-phenylamino-4'''-(N-methyl-beta-hydroxy-ethylamino)-s-triazinyl-(6''')-amino]stilbene-2,2'-disulfonic acid, by heating an aqueous slurry of it containing sufficient electrolyte to keep the optical brightener out of solution to between 100° and 200° C. This patent notes that the procedure of United Kingdom Pat. No. 997,044 is not directly applicable to this compound; in particular it recommends against the presence of the electrolyte which is critical to the procedure of this patent stating it may inhibit the formation of the desired crystal form.

U.S. Pat. No. 3,511,833 discloses an alternate procedure for modifying this same compound by refluxing a slurry of this brightener in an aqueous medium containing both a water soluble organic solvent and sufficient sodium based electrolyte to keep the brightener out of solution. This patent also discloses heating a similar slurry to temperatures as low as 60° C. when seed crystals of the desired crystal form are added.

U.S. Pat. No. 3,925,260 discloses the crystal modification of several sodium N,N'-bis-[4-anilino-6-(2-alkoxyalkyl amino)-1,3,5-triazin-2-yl]-4,4'-diamino stilbene-2,2'-disulphonates by holding an aqueous solution of the particular brightener containing between 1 and 2.5 volume percent of sodium based electrolyte at 20° to 70° C. The solution pH is above 7 and seed crystals are typically added. An alternative procedure similar to U.S. Pat. No. 3,511,833 is also disclosed; heating of the brightener in an aqueous medium containing table salt and an organic solvent.

U.S. Pat. No. 3,994,834 discloses that 4,4'-bis-[4-phenyl-v-triazolyl-(2)]-stilbene-2,2'-disulfonic acid must be converted to the potassium salt form to obtain suitable crystal forms. The suitable crystal forms are obtained by heating to temperatures between 50° and 150° C. in the presence or absence of an aqueous alcohol.

U.K. Pat. No. 1,293,804 is concerned with the crystal modification of sodium 4,4'-bis-[4-anilino-6-(bis(2-hydroxyethyl)-amino)-1,3,5-triazin-2-yl]-amino-stilbene-2,2'-disulfonate by heating it in an aqueous medium containing an organic solvent and a sodium based electrolyte. The procedure exemplified utilizes seed crystals and refluxes the water solvent mixture. No indication is given of the necessary temperature for a seed free process.

U.K. Pat. No. 773,152 is concerned with the production of the same optical brightener as U.S. Pat. Nos. 3,472,842 and 3,511,833 but it obtains the yellow colored crystal form which these later patents disfavor. Its preparative technique exposes the sodium salt to temperatures of 90° to 95° C. during the final synthesis step. It is not clear if the compound is in solution at this point.

U.K. Pat. No. 1,173,806 discloses forming a number of optical brighteners of low water solubility into hollow beads. The beads are formed by spray drying an aqueous slurry of the optical brightener using outlet temperatures between 65° and 90° C. Among the suitable brighteners listed is the free acid form of the compound with which the present invention is concerned; 4,4'-bis-[2-anilino-4-methylaminotriazinyl-6-amino]-stilbene-2,2'-disulphonic acid. Presumably, the sodium salt is not listed because it has a rather high water solubility.

Japanese Patent Publication No. 5880/59 discloses the preparation of the precise compound with which the present invention is concerned. It isolates the sodium salt form of this optical brightener after exposing it to a temperature of about 70° C. during the last synthesis step. It is not clear whether this compound is in solution or slurry at this point. Nothing is said about the crystal form of the recovered product.

The commercial production of the free acid form of this optical brightener has been conducted in the United States. The synthesis involved the exposure of the sodium salt form to temperatures in excesses of 90° C. but this salt was never isolated on a commercial basis because its high water solubility would cause unacceptable yield losses on filtering.

SUMMARY OF THE INVENTION

The present invention comprises a new modification of the optical brightener of the following structure:

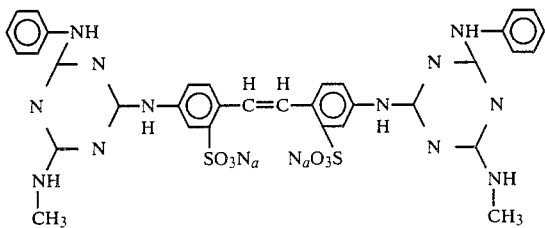

known as sodium 4,4'-diamino-bis-(2-anilino-4-methylamino-1,3,5-triazinyl-6-amino)-stilbene-2,2'-disulphonate and a procedure for obtaining this modification. This modification is characterized by Debye-Scherrer X-ray pattern reflections of the following relative intensities representative of the following d-spacings:

| Relative Intensity | d-Spacing (in Å) |
|---|---|
| Fairly strong | 8.18–8.35 |
| Fairly strong | 7.14–7.25 |
| Fairly strong | 5.22–5.28 |
| Strong | 4.72–4.80 |
| Weak | 4.57 |
| Fairly strong | 3.53–3.59 |
| Moderate | 3.38–3.40 |

This modification is also characterized by the fact that it does not discolor a detergent with which it is slurried at a ratio of 1 part to 200 parts detergent after drying at 85° to 90° C. The modification may be obtained by heating an aqueous slurry of this compound at a temperature in excess of 65° C., preferably in excess of 90° C. in the presence of sufficient electrolyte to prevent the total dissolution of the compound at the treatment temperature.

BRIEF DESCRIPTION OF THE DRAWINGS

FIGS. 1 and 2 are Debye-Scherrer X-ray diffraction patterns of modifications made in accordance with Example 1. FIG. 1 is representative of a material spray dried with an outlet temperature of about 65° C. to give a slightly yellow powder while FIG. 2 is representative of a material spray dried with an outlet temperature of 110° C. to give an orange yellow powder. Both patterns were generated using K alpha copper radiation having a wavelength of 1.5418 angstroms. The absissa records the Bragg angle, 2 theta, in degrees and the ordinate records the relative intensity of the reflections. FIG. 1 had this relative intensity twice as magnified as FIG. 2.

DETAILED DESCRIPTION OF THE INVENTION

The new modification has a distinct crystal phase but its precise definition is difficult. The particle size of the dried modified material makes it difficult to obtain a sharp Debye-Scherrer X-ray diffraction pattern. Thus, the precise location of some of the stronger peaks and the existence of some of the weaker peaks are difficult to ascertain. However, on X-ray analyses of different samples, a clearly recognizable pattern is obtained.

The new modification is also characterized by its coloration both upon drying and upon subsequent slurrying and redrying. This modification will give an essentially white powder if it is dried at temperatures between 60° and 70° C. At drying temperatures of about 110° C. it gives a yellow colored powder. However, if material initially dried at between 60° and 70° C. is reslurried and then dried at 110° C. it remains white. On the other hand, if material initially dried at 110° C. is reslurried and then dried at 60° to 70° C. it yields a white powder.

The new modification does not cause discoloration of dry detergent compositions prepared by slurrying the components in water and drying. In particular, if optical brightener dried to either a yellow or a white powder is slurried at a ratio of 1 part by weight to 200 parts by weight of detergent in water and dried at 85° to 90° C. the color is indistinguishable from a dried slurry of detergent alone.

The optical brightener modification of the present invention may be obtained by heating an aqueous slurry of the sodium salt form of this bis-triazinyl amino stilbene compound to a temperature in excess of 65° C., preferably in excess of 90° C. The slurry should be held at temperature for a period sufficient to convert all the undissolved brightener to the new crystal form. A period of four hours at temperature is usually more than adequate.

The pH of the aqueous slurry should be controlled to be no less than neutral. Otherwise some of the sulphonate groups of the brightener may revert to their free acid form. It is preferred to keep the pH alkaline and a pH in excess of about 10.5 is especially preferred.

This process does not require the presence of any organic solvents or the use of elevated pressures. Thus, the modified brightener may be recovered directly from the treatment bath by spray drying without posing an explosion risk. The treatment itself may be conducted in conventional equipment at atmospheric pressure.

The brightener may be conveniently heated in an aqueous solution of an electrolyte. Sufficient electrolyte should be included to prevent the complete dissolution of the brightener at the treatment temperature. Any electrolyte which will not adversely effect the brightener may be used. In order to avoid the possibility of changing the nature of the counter ion to the brightener's sulfonic acid groups sodium based electrolytes are preferred. The sodium salts of the mineral acids are particularly preferred. Trisodium phosphate is an especially preferred electrolyte. If an aqueous slurry containing about 33% of optical brightener is to be treated, the addition of at least about 10 wt. % of electrolyte based on the weight of the slurry has been found to give good results.

The treatment bath may also contain a dedusting agent. Between about 2 and 6 wt. %, based on the weight of optical brightener, may be conveniently used.

In a preferred embodiment the new modification optical brightener is recovered by spray drying. The treatment slurry including the electrolyte is fed to a spray dryer after being held at the treatment temperature for a sufficient time to obtain the new modification. The spray dryer may have any convenient inlet temperature and temperatures between about 220° and 370° C. were found suitable. However, if an initially white product is desired, the outlet temperature should be kept at below about 80° C., preferably below about 75° C. Depending on the particular equipment used this outlet temperature requirement will limit the maximum inlet temperature; the faster the feed rate which can be sustained, the greater the spread between inlet and outlet temperature may be.

This procedure provides a high yield of the rather strongly water soluble sodium salt and at the same time it provides an already standardized product. The recovery of this sodium salt by filtration has been found to result in yield losses of as much as 10%. The electrolyte to optical brightener ratio established in the treatment bath will be retained after spray drying so the concentration of active ingredient in the spray dried product can be readily controlled. Further, the amount of electrolyte added to the bath may be adjusted in accordance with the spectral strength of the optical brightener being converted; the crystal modification obviously does not effect its properties in solution.

The following examples illustrate the invention without limiting it in any way.

EXAMPLES

Example 1

Preparation of the Disodium Salt

A sufficient amount of the presscake of 4,4'-bis-[2-methylamino-4-phenylamino-1,3,5-triazinyl-(6)-amino]-stilbene-2,2'-disulphonic acid and water were charged to a vessel to give a slurry with a solids concentration of 33%. This slurry was heated to 70° to 75° C. Sufficient 50% NaOH solution was added to adjust the pH to between 11 and 11.5 at a rate slow enough to avoid the formation of lumps. The presscake solids went into solution.

Preparation of the New Modification

The solution of the disodium salt was heated to between 90° and 95° C. over a period of two hours holding the pH constant. Then 0.382 parts of trisodium phosphate per part of presscake solids were added over a period of two hours. As this electrolyte was added a brown, sticky scum formed which then dissolved. The bath was held at 90° to 95° C. for a period of four hours during which the optical brightener crystallized and formed a white slurry.

Recovery of the New Modification

The new modification was recovered in four different manners. In two cases it was fed to a spray dryer and in two cases it was trapped on a filter and vacuum dried. A combination of 3.1 parts of white mineral oil and 1.5 parts of sulphonated mineral oil per 100 parts of presscake solids were added to the spray drier feed line as a dedusting package. The resulting powders had the following appearances:

| Spray Dried | | Vacuum Dried | |
|---|---|---|---|
| Outlet temp. of 75° C. | Outlet temp. of 110° C. | 60° C. | 110° C. |
| white or ivory | canary yellow | white | yellowish |

All four of these materials had essentially the same Debye-Scherrer X-ray diffraction pattern using a copper K alpha radiation. Furthermore, all four of these materials caused no discoloration when slurried with detergent at a weight ratio of 1 part to 200 parts detergent and then dried at 85° to 90° C.

Example II

A reaction slurry obtained from the commercial synthesis of the free acid form of the optical brightener of the present invention and having a solids content of about 11% was treated in the same manner as the presscake slurry of Example I except that it was only recovered by spray dyring with an outlet temperature of 75° C. A white powder was obtained.

Example III

A 33% slurry of the free acid form of the optical brightener was prepared and neutralized as in Example I. The trisodium phosphate, 0.382 parts per part of presscake solids, was added at 70° C. The bath was held at this temperature for six hours. The compound was all converted to the new crystalline form. The slurry was then spray dried using an outlet temperature of 75° C. A trace yellow powder was obtained.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A new crystal form of the sodium salt form of the optical brightener having the following structure

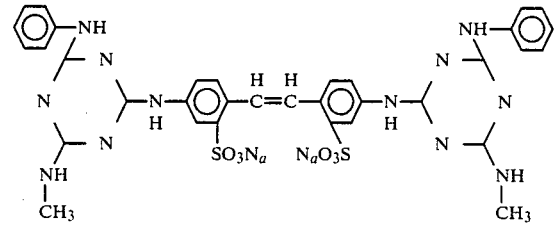

said crystal form being characterized by Debye-Scherrer X-ray diffraction pattern reflections of the following relative intensities representative of the following d-spacings:

| Relative Intensity | d-Spacing (in Å) |
|---|---|
| Fairly strong | 8.18–8.35 |
| Fairly strong | 7.14–7.25 |
| Fairly strong | 5.22–5.28 |
| Strong | 4.72–4.80 |
| Weak | 4.57–4.58 |
| Fairly strong | 3.53–3.59 |
| Moderate | 3.38–3.40 |

2. A process for obtaining a crystalline form of sodium-4,4'-bis-(2-anilino-4-phenylamino-1,3,5-triazinyl-6-amino)-stilbene-2,2'-disulphonate which is white on drying from an aqueous slurry at 75° C. or less and displays fairly strong to strong Debye-Scherrer X-ray diffraction pattern reflections representative of d-spacings at 8.18–8.35, 7.14–7.25, 5.22–5.28, 4.72–4.80 and 3.53–3.59 angstroms comprising heating an aqueous slurry containing at least some of this compound in undissolved form at a temperature above about 65° C. for a time sufficient to substantially convert this compound to this crystalline form.

3. The process of claim 2 wherein the aqueous medium contains sufficient dissolved electrolyte to ensure that at least some of said compound remains undissolved at the treatment temperature.

4. The process of claim 3 wherein the electrolyte is based upon sodium.

5. The process of claim 4 wherein the electrolyte is a salt of sodium and a mineral acid.

6. A process for obtaining a crystalline form of sodium-4,4'-bis-(2-amino-4-phenylamino-1,3,5-triazinyl-6-amino)-stilbene-2,2'-disulphonate which is white on drying from an aqueous slurry at 75° C. or less and displays fairly strong to strong Debye-Scherrer X-ray diffraction pattern reflections representative of d-spacings at 8.18–8.35, 7.14–7.25, 5.22–5.28, 4.72–4.80 and 3.53–3.59 angstroms comprising the steps of:
(a) heating an aqueous slurry containing an electrolyte and at least some of this compound in undissolved form at a temperature above about 60° C.; and
(b) spray drying this slurry to obtain the compound and electrolyte as a dry powder.

7. The process of claim 6 wherein the spray dryer outlet temperature is less than about 80° C. and the recovered powder is white in color.

8. The process of claim 6 wherein the solids content of the slurry is less than about 40%.

9. The process of claim 6 wherein the ratio of said compound to electrolyte is less than about 3:1.

10. The process of claim 9 wherein the electrolyte is trisodium phosphate.

11. The process of claim 6 wherein the outlet temperature of the spray dryer is high enough to give a yellow colored powder and this powder is subsequently slurried in water and dried to give a white powder at a temperature less than about 80° C.

12. The process of claim 2 or 6 wherein the pH of the aqueous slurry is maintained at an alkaline value during the heating.

13. The process of claim 2 or 6 wherein the pH of the aqueous slurry is maintained at a pH of greater than about 10.5.

* * * * *